United States Patent
Donadille et al.

(10) Patent No.: US 10,393,641 B2
(45) Date of Patent: Aug. 27, 2019

(54) METHODS OF DETERMINING CEMENTATION EXPONENT AND SATURATION EXPONENT IN POROUS MEDIA FROM DIELECTRIC DISPERSION DATA

(71) Applicant: SCHLUMBERGER TECHNOLOGY CORPORATION, Sugar Land, TX (US)

(72) Inventors: Jean-Marc Donadille, Clamart (FR); Lalitha Venkataramanan, Lexington, MA (US); Vasileios-Marios Gkortsas, Boston, MA (US); Stacy Lynn Reeder Blanco, Littleton, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 241 days.

(21) Appl. No.: 14/962,201

(22) Filed: Dec. 8, 2015

(65) Prior Publication Data

US 2017/0123104 A1    May 4, 2017

Related U.S. Application Data

(60) Provisional application No. 62/248,679, filed on Oct. 30, 2015.

(51) Int. Cl.
*G01N 15/08* (2006.01)
*G01V 3/32* (2006.01)
(Continued)

(52) U.S. Cl.
CPC .......... *G01N 15/088* (2013.01); *G01N 33/24* (2013.01); *G01V 3/06* (2013.01); *G01V 3/32* (2013.01); *E21B 49/00* (2013.01)

(58) Field of Classification Search
CPC ............................ G01V 11/002; G01N 15/088
(Continued)

(56) References Cited

U.S. PATENT DOCUMENTS

| | | | |
|---|---|---|---|
| 2003/0105590 A1* | 6/2003 | Mollison | G01V 3/28 702/7 |
| 2009/0177403 A1* | 7/2009 | Gzara | E21B 49/008 702/7 |

(Continued)

OTHER PUBLICATIONS

Abdel Aal, A. F. et al., "Integration of Dielectric Dispersion and 3D NMR Characterizes the Texture and Wettability of a Cretaceous Carbonate Reservoir", SPE 164150, presented at the SPE Middle East Oil and Gas Show and Conference, Manama, Bahrain, 2013, 12 pages.

(Continued)

*Primary Examiner* — Ricky Ngon

(57) ABSTRACT

Methods are provided for determining values of a pore cementation exponent m and/or a saturation exponent n for locations in a formation having similar petrophysical properties. Formation porosity, formation water saturation, and an apparent cementation exponent $m_n$ are obtained for the locations and their values are utilized to find the exponents. In one embodiment, the apparent cementation exponent and the formation water saturation are obtained from a dielectric logging tool.

20 Claims, 6 Drawing Sheets

(51) Int. Cl.
*G01V 3/06* (2006.01)
*G01N 33/24* (2006.01)
*E21B 49/00* (2006.01)

(58) Field of Classification Search
USPC .......................................................... 702/7
See application file for complete search history.

(56) References Cited

U.S. PATENT DOCUMENTS

| | | | |
|---|---|---|---|
| 2011/0060526 A1* | 3/2011 | Faivre | G01V 5/104 |
| | | | 702/8 |
| 2012/0192640 A1* | 8/2012 | Minh | E21B 7/06 |
| | | | 73/152.16 |
| 2014/0114576 A1 | 4/2014 | Jain et al. | |

OTHER PUBLICATIONS

Venkataramanan, L. et al., "Experimental Study of the Effects of Wettability and Fluid Saturation on Nuclear Magnetic Resonance and Dielectric Measurements in Limestone", Petrophysics, 2014, 55(6), pp. 572-586.

Jain, V., et al., "Characterization of Underlying Pore and Fluid Structure Using Factor Analysis on NMR Data", SPWLA 54th Annual Logging Symposium, 2013, pp. 1-16.

Ramamoorthy, R. et al., "A New Workflow for Petrophysical and Textural Evaluation of Carbonate Reservoirs", SPWLA 49th Annual Logging Symposium, 2008, pp. 1-15.

* cited by examiner

| CORES A AND B | CORE | $m_n$ | $S_w$ |
|---|---|---|---|
| 100% WATER SATURATION | A | 2.04 | 1 |
| | B | 2.05 | 1 |
| PRIMARY DRAINAGE | A | 2.8 | 0.22 |
| | B | 2.9 | 0.21 |
| SPONTANEOUS IMBIBITION | A | 2.7 | 0.14 |
| | B | 3.3 | 0.05 |
| FORCED IMBIBITION | A | 2.6 | 0.52 |
| | B | 2.7 | 0.52 |
| SPONTANEOUS DRAINAGE | A | 3.2 | 0.31 |
| | B | 4.97 | 0.4 |

METHODS OF DETERMINING CEMENTATION EXPONENT AND SATURATION EXPONENT IN POROUS MEDIA FROM DIELECTRIC DISPERSION DATA

PRIORITY

The present application claims the benefit of U.S. Application Ser. No. 62/248,679 filed Oct. 30, 2015, which application is incorporated herein, in its entirety, by reference.

TECHNICAL FIELD

The subject disclosure relates to the investigation of geological formations. More particularly, the subject disclosure relates to methods of determining cementation exponent and saturation exponent of a porous medium via the use of dielectric dispersion data gathered from the medium. The subject disclosure has particular application to oilfield exploration and exploitation although it is not limited thereto.

BACKGROUND

In analyzing and developing oilfields, it is common to drill wellbores in the formation containing a hydrocarbon reservoir for the purpose of running tools down the wellbore(s) in order to generate data useful in analyzing the makeup of the formation and the contents of the reservoir. Some of the commonly run tools include resistivity tools, spectroscopy tools, and dielectric scanning tools. Nuclear magnetic resonance (NMR) tools and acoustic tools are also often run. The data obtained from the tools are regularly used to analyze and model the geological formation and the reservoir. Information regarding the rock matrix and the fluid volume, such as porosity, permeability, hydrocarbon volume, water and oil saturations, conductivities, etc., are desired results.

Interpretation models are used to estimate water saturation $S_w$, water salinity, and an effective cementation exponent $m_n$ from measured dielectric data. The parameter $m_n$ is known to combine multiple effects including the effect of pore space tortuosity, which is captured by a cementation exponent m, and the distribution of water and hydrocarbons in the pore system, which is captured by a saturation exponent n in the well-known Archie's equation.

Parameter $m_n$ has several applications. When the value of m can be estimated through measurements such as measurements from a nuclear magnetic resonance (NMR) tool or from a full bore micro resistivity imager tool, such as FMI-HD™ (a trademark of Schlumberger Technology Corporation), or from core resistivity measurements, the parameter $m_n$ may be used to estimate n which can then be used to infer information about wettability. In addition, $m_n$ obtained in a shallow (e.g., invaded) zone by downhole dielectric tools is used to estimate water saturation in the deep (e.g., virgin) zone using deep resistivity tools and Archie's law. These applications, however, are limited in scope for several reasons. First, NMR, micro resistivity imager, or core measurements may not be available to provide a value for parameter m. Second, due to mud invasion in the formation, water saturation values in the shallow and deep zones are likely to be different. Since $m_n$ is saturation dependent, an invaded zone $m_n$ can be used to derive water saturation in the virgin zone only if their saturations are the same or when m=n.

SUMMARY

Illustrative embodiments of the present disclosure are directed to methods of determining cementation exponent m and/or saturation exponent n at multiple depths (i) in a formation. The cementation exponent m and/or the saturation exponent n are obtained utilizing values, at those formation depths, of the apparent cementation exponent $m_n$ obtained from a dielectric tool, and from determined or known values of water saturation $S_w(i)$ and porosity $\phi(i)$ at those depths.

In various embodiments, the cementation exponent m and saturation exponent n values may be used for, among many applications, inferring wettability, estimating water saturation in virgin zones, and choosing relative permeability curves for dynamic reservoir modeling.

In illustrative embodiments, the cementation exponent m and the saturation exponent n at a depth i in a formation are determined by gathering data from depth intervals of similar petrophysical properties using the data to provide points on a plot comparing $m_n$ and a, where $a=\log(\phi)/(\log(\phi)+\log S_w)$, and fitting a line of slope m−n to the points on the plot, such that m is found at the intersection of the line and a=1, and n is found at the intersection of the line and a=0.

In another embodiment, rather than generating points, fitting a line to the points, and locating intersections, the values m and n are found using linear algebra and computations which accomplish the equivalent.

In some embodiments, the uncertainty underlying the gathered data is used in calculating the indications of m and n.

In a further illustrative embodiment, depth intervals of similar petrophysical properties may be obtained by classifying rock (formation) intervals based on rock typing or classification using their NMR signal response. For each depth interval, a pore cementation exponent m and/or a saturation exponent n is determined using the formation porosity, formation water saturation, and the apparent cementation exponent. In one such embodiment, an NMR technique called "factor analysis" is used to identify locations of similar petrophysical properties. In another embodiment, an NMR technique called "P3A," which divides the $T_2$ transverse relaxation NMR signal into three segments representing micro-pores, meso-pores and macro-pores, may be used to identify locations of similar petrophysical properties.

Additional aspects, embodiments, objects, and advantages of the disclosed methods may be understood with reference to the following detailed description taken in conjunction with the provided drawings.

DETAILED DESCRIPTION

Before turning directly to the embodiments of the method, a technical discussion regarding the parameters of interest is useful for understanding the embodiments.

One parameter that is obtained upon analyzing data from downhole tools such as dielectric and NMR tools (e.g., using interpretation software) is $m_n$. This parameter is often called an "apparent cementation exponent". More particularly, $m_n$ is a textural parameter that is obtained from inversion of the complex permittivity dispersion measured downhole (and in labs). The forward models used in this inversion are often bimodel and Stroud-Milton-De (SMD) models. The predicted conductivity from these models tends to the Archie formulation with $m_n=m=n$ at a low frequency (DC limit) according to:

$$\sigma = (\phi S_w)^{m_n} \sigma_w \qquad (1)$$

where $\sigma$ is the measured conductivity of the partially saturated rock with porosity $\phi$ and water saturation $S_w$, $\sigma_w$ is the DC conductivity of the water, and $m_n$ is the apparent cementation exponent that combines two effects: (i) the effect of pore space tortuosity which is captured by cementation exponent m, and (ii) the distribution of water and hydrocarbons in the pore system which is captured by the saturation exponent n.

Combining Archie's law below, $$\sigma = \phi^m S_w^n \sigma_w, \qquad (2)$$

with equation (1), the following is obtained:

$$(\phi S_w)^{m_n} = \phi^m S_w^n. \qquad (3)$$

It should be appreciated that unless m=n, there is no constant $m_n$ that will satisfy equation (3) for all saturations. Therefore, $m_n$ may be considered a function of water saturation. Equation (3) may be re-written as:

$$m_n = \frac{m\log(\phi) + n\log(S_w)}{\log(\phi) + \log(S_w)}. \qquad (4)$$

Figure 1A:
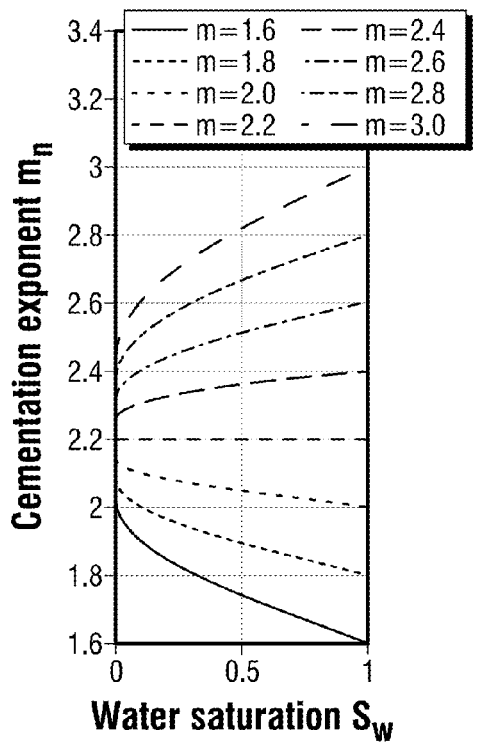
FIGS. 1A and 1B are respectively plots of a cementation exponent $m_n$ as a function of water saturation (i) for values of pore cementation exponent m with fixed porosity and fixed saturation exponent n and (ii) for values of n with fixed porosity and fixed m.
Figure 1B:
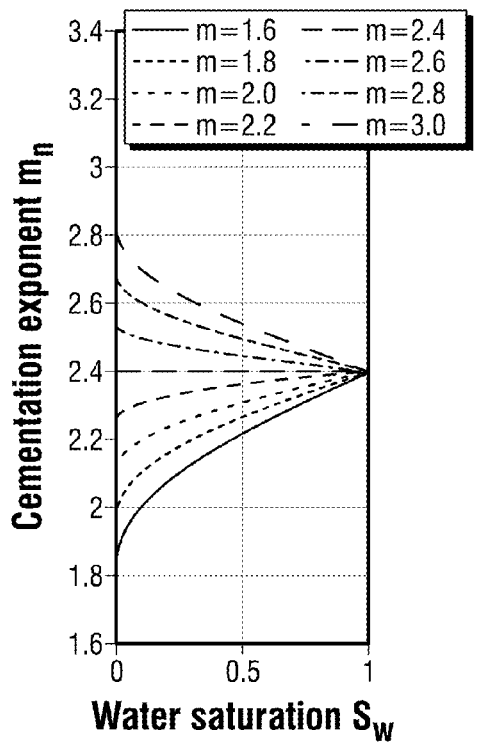

From equation (4), it is clear that in a water zone, when $S_w=1$, that $m_n=m$, and that in a hydrocarbon zone, where $S_w$ is close to zero, $m_n$ approaches n. This confirms that the parameter $m_n$ is a function of water saturation and varies between n when $S_w$ approaches 0 and m when $S_w=1$. In a zone with partial oil and water saturations, $m_n$ takes an intermediate value between m and n. FIG. 1A shows $m_n$ as a function of water saturation for various m values (assuming fixed porosity $\phi=0.2$ and fixed n value=2.2), while FIG. 1B shows m as a function of water saturation for various n values (assuming fixed porosity $\phi=0.2$ and fixed m value=2.4).

Among other known uses, parameter m is used to compute virgin zone water saturation and estimate wettability. Sometimes, a value for parameter $m_n$ is simply assumed (e.g., $m_n=1.8$ or $m_n=2.0$). In other cases, values for m are estimated from dielectric measurements which are generally sensitive to fluid and rock properties in the invaded zone of a formation around a wellbore. More particularly, in order to compute virgin zone water saturation, $m_n$ is used in conjunction with knowledge of the porosity and the ratio of the bulk water conductivity to water conductivity according to Archie's law of equation (1) rewritten as:

$$S_w = \frac{1}{\phi}\left(\frac{\sigma}{\sigma_w}\right)^{1/m_n}. \qquad (5)$$

Again, it should be appreciated that the value of $m_n$ used in equation (5) is obtained from dielectric dispersion measurements in the invaded zone. However, using the invaded zone m value for deriving the saturation in the virgin zone rests on the generally incorrect assumption that $m_n$ is either saturation independent with m=n, or that the virgin zone water saturation is the same as the invaded zone saturation.

Parameter m is likewise used to estimate wettability based on a rewriting of equation (3) according to:

$$n = \frac{(m_n - m)\log(\phi) + m_n\log(S_w)}{\log(S_w)}, \qquad (6)$$

where the porosity and water saturation are known, and the pore cementation exponent m is assumed or estimated from sources, such as from an NMR analysis, from a formation micro resistivity imager tool, or from laboratory core study. The exponent n was estimated in this manner in Abdelaal, A. F., et al., Integration of Dielectric Dispersion and 3D NMR characterizes the Texture and Wettability of a Cretaceous Carbonate Reservoir, SPE 164150 (2013), and can be used to infer wettability of the formation. However, estimating n in this manner requires an independent measurement for the estimation of parameter m.

According to one aspect, values for both m and n of a rock sample may be determined through knowledge of the porosity and water saturation of that rock sample and from dielectric dispersion measurements. Stated in another way, values for both m and n may be determined together without pre-knowledge of the other. In particular, let i denote an index in a set of measurements where the cementation exponent m and the saturation exponent n are expected or assumed to be constant. In surface core measurements, these sets of measurements may correspond to measurements of different saturation stages of a core, measurements on different cores of similar lithology but varying porosity in the same saturation stage, or measurements on different cores with similar Archie parameters but different water saturations and porosities. In downhole data, and as will be discussed hereinafter with respect to particular NMR measurements that may be made for this purpose, this set of measurements may correspond to a depth interval or depth intervals or points with similar petrophysical properties.

Thus, according to one embodiment, equation (4) is rewritten as $$m_n(i) = (m-n)a(i) + n, \quad (7)$$

where $m_n(i)$ is the estimated $m_n$ at depth i and may be obtained from a dielectric measurement, and $$a(i) = \frac{\log(\phi(i))}{\log(\phi(i)) + \log(S_w(i))} \quad (8)$$

which may be computed from porosity and water saturation measurements. From equation (8), it will be appreciated that when $S_w(i)=1$, $a(i)=1$ and $m_n=m$. Also, when $S_w(i)=0$, $a(i)=0$ and $m_n=n$. Therefore, in an $m_n$-a crossplot, the data points corresponding to different depths should lie on a straight line with slope (m−n) and intersecting the a=1 and a=0 axes at m and n, respectively.

In one embodiment, parameters m and n over a depth interval i (or over locations having similar petrophysical properties and given index i) can be estimated according to:

$$\begin{bmatrix} \Sigma a^2(i) & \Sigma a(i)(1-a(i)) \\ \Sigma a(i)(1-a(i)) & \Sigma((1-a(i))^2 \end{bmatrix} \begin{bmatrix} m \\ n \end{bmatrix} = \begin{bmatrix} \Sigma a(i)m_n(i) \\ \Sigma(1-a(i))m_n(t) \end{bmatrix}. \quad (9)$$

For increased robustness, equation (9) can be extended to include weights w(i) at each depth according to:

$$\begin{bmatrix} \Sigma w(i)a^2(i) & \Sigma w(i)a(i)(1-a(i)) \\ \Sigma w(i)a(i)(1-a(i)) & \Sigma w(i)((1-a(i))^2 \end{bmatrix} \quad (10)$$

$$\begin{bmatrix} m \\ n \end{bmatrix} = \begin{bmatrix} \Sigma w(i)a(i)m_n(i) \\ \Sigma w(i)(1-a(i))m_n(t) \end{bmatrix}.$$

For example, the weights can be set as the inverse of the uncertainty associated with the $m_n$ value, which may have been computed during the inversion of the dielectric measurements.

Figure 2A:
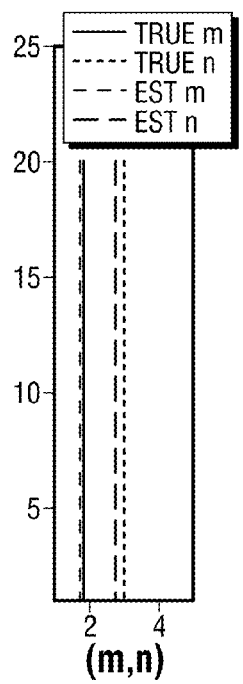
FIGS. 2A-2D are simulated well logs of true and calculated values for Archie parameters m and n, porosity, water saturation of an invaded zone, and water saturation of a virgin zone, respectively.
Figure 2B:
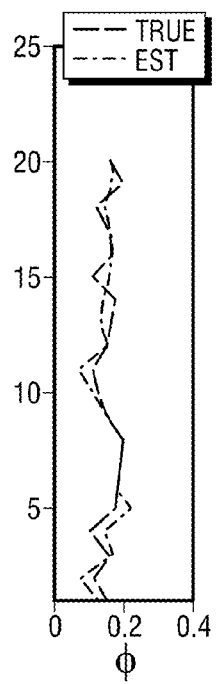
Figure 2C:
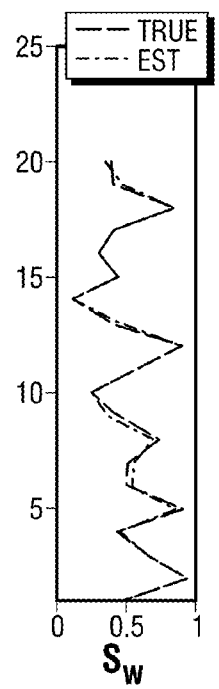
Figure 2D:
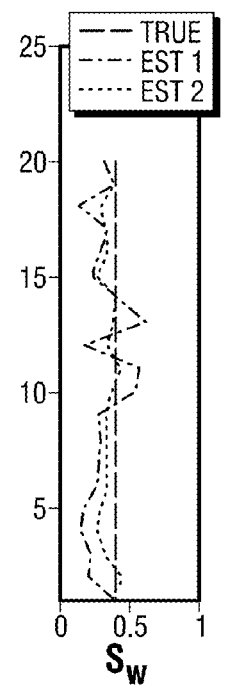

Results of simulations utilizing equation (9) are shown in FIGS. 2A-2D and FIG. 3. More particularly, in the simulation, over a depth interval, "true" values for Archie parameters m and n were assigned (as constants over the zone) as seen in FIG. 2A, and "true" values for porosity, the water saturation in the invaded zone, and the water saturation in the virgin zone were assigned as seen in FIGS. 2B-2D respectively, with the porosity and invaded zone water saturation varying, and the virgin zone water saturation (FIG. 2D) set to a constant value of 0.4 over the zone. Assuming a 2 pu (porosity unit) uncertainty in porosity, a 10% variation in estimated $S_w$ in the invaded zone from the true value, and a variation of 10% in $m_n$ from its true value computed using equation (3), data points were generated (e.g., using a Monte Carlo algorithm), and the Archie parameters m and n were estimated (calculated) using equation (9) to provide a value of m approximately equal to 1.7 and a value of n approximately equal to 2.7. The estimations for m and n are shown in FIG. 2A and are seen to be close to their true values. In addition, estimations for porosity (e.g., from NMR data) and invaded zone water saturation (e.g., from dielectric measurements or NMR data) are shown in FIGS. 2D and 2C and correspond closely with the true values. Further, the virgin zone water saturation was calculated using a conventional technique, where an estimated $m_n$ from the invaded zone is used to estimate virgin zone water saturation according to equation (5) (shown as Est 1 in FIG. 2D), and according to the present method (shown as Est 2 in FIG. 2D), where the estimated values of m and n (as determined from equation (9)) are used according to Archie's equation set forth in equation (2) above. As seen in FIG. 2D, in various embodiments, the present method provides a result that is significantly more accurate (smaller error) and more robust (smaller standard deviation) than the conventional method.

Figure 3:
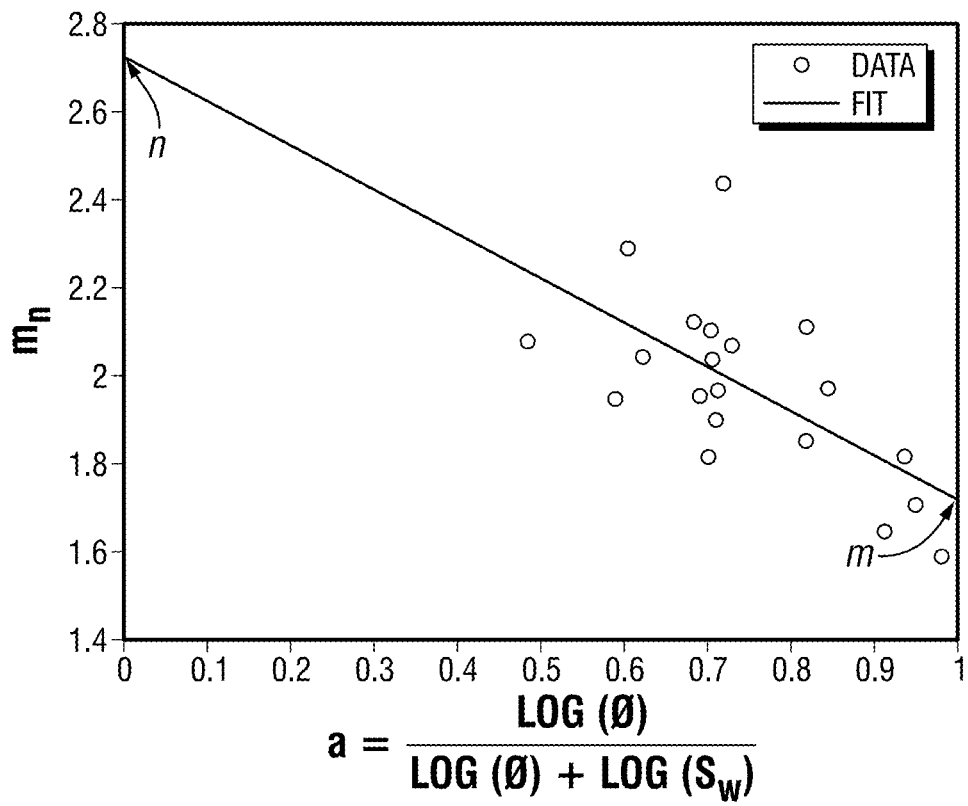
FIG. 3 is a plot of points taken from the data of the simulated logs of FIGS. 2A-2D and plotted relative to values of $m_n$ and a, which is a function of porosity and water saturation, with a line fit to the points and providing values for m and n.

The generated data points were also plotted in FIG. 3 on a plot having variable parameter a from equation (8) as the x-axis and $m_n$ as the y-axis. A line was fit to the data points using a least squares fit, and as seen in FIG. 3, the n value (of approximately 2.7) is obtained by the intersection of line with the a=0 axis, and the m value (of approximately 1.7) is obtained by the intersection of the line with the a=1 axis.

Figure 4:
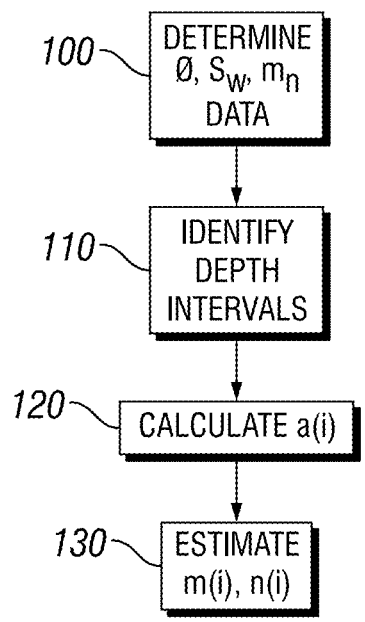
FIG. 4 is a flow chart that shows a method in accordance with one embodiment of the present disclosure.

Turning to FIG. 4, a method according to one embodiment of the present disclosure is shown. More particularly, at 100, formation data at multiple depths are obtained using wellbore tools. For example, a log of $m_n$ values is obtained (with associated uncertainties) and a log of invaded zone water saturations $S_w$ is obtained using a dielectric tool, such as a Dielectric Scanner™ tool with Dielectric Pro™ software (both trademarks of Schlumberger Technology Corporation). A log of porosities is obtained using a neutron porosity tool, such as a CNT™ tool or a SCNT™ tool, or an NMR porosity tool, such as the CMR-Plus Tool™ (all trademarks of Schlumberger Technology Corporation), or using other tools or processing.

At 110, depth intervals with similar petrophysical properties are identified (as discussed in more detail hereinafter) to generate a series of indices i, and at 120, the porosity and water saturation data points associated with each index i are used to calculate values for a(i). At 130, values for a(i) and $m_n(i)$ are then used to determine values for m and n for that depth interval (i.e., m(i), n(i)). More particularly, in some embodiments, equation (9) is used at 130 to calculate m and n. In some embodiments, where uncertainties associated with the $m_n$ value is obtained, equation (10) is used at 130 to calculate m and n (the weights w(i) in equation (10) are related to the uncertainties, typically by being the inverses of the uncertainties). In some embodiments, for each depth in the interval, a(i), $m_n$ points are generated, optionally plotted, and fit to a line (as in FIG. 3) in order to provide m and n estimates. It will be appreciated that steps 120 and 130 are repeated for each depth interval (or group of locations) to generate m and n values for that depth interval. At 140, the m and/or n values are used for any of many purposes, such as inferring wettability, estimating water saturation in virgin zones (e.g., using equation (2)), and choosing relative permeability curves for dynamic reservoir models used in simulation and prediction of production and effectiveness of stimulation, etc. The m and n values may also be plotted as a function of depth (e.g., as in a well log).

Figures 5, 6:
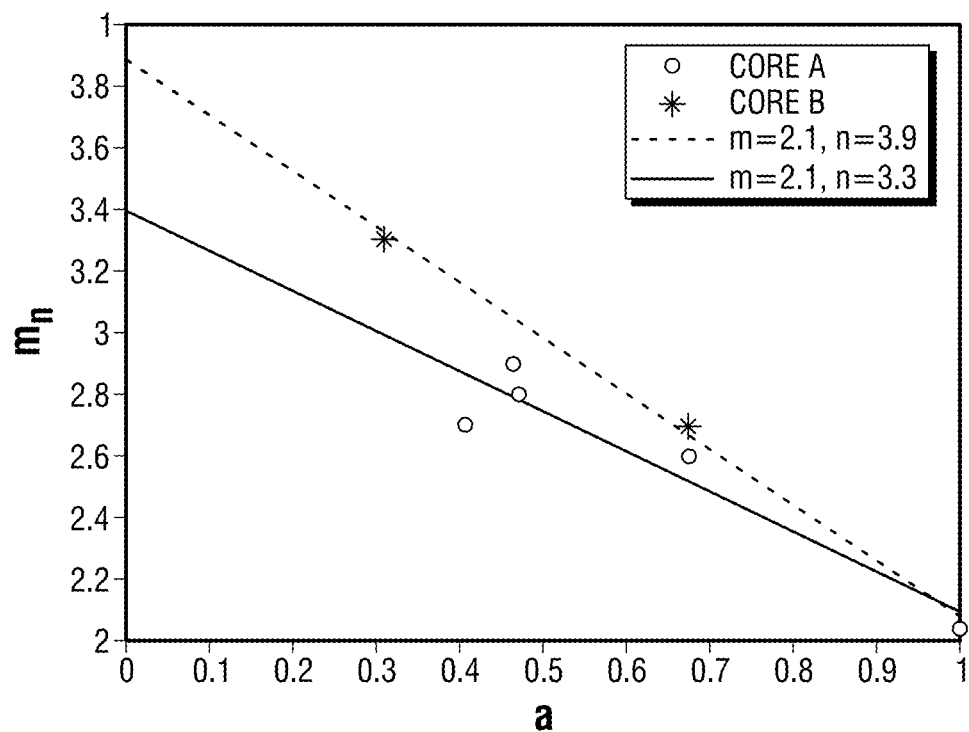
FIG. 5 is a table showing results of a bimodal model to data at different saturation stages on two cores having identical lithology but different wettability.
FIG. 6 is a plot with axes of apparent cementation exponent $m_n$ and parameter a, with lines fit to points and showing the cores identified in FIG. 5 having the same cementation exponent m but different values for exponent n due to different wettability.

Laboratory measurements on two cores were made to validate the methods described herein. Two cores of identical lithology were obtained in a laboratory, and with a specialized protocol, one core (core "B") was designed to be more mixed-wet than the other core (core "A"). Dielectric data were obtained from both cores at different saturation stages with varying amounts of water saturation and analyzed with a bimodal dielectric model to estimate both $m_n$ and $S_w$, which are displayed in the table of FIG. 5. Two observations are evident from this table. First, for core A, the estimated $m_n$ varies with $S_w$. Second, $m_n$ for core B is larger than for core A. Since $m_n$ is a function of both wettability and saturation, it is impossible to associate the variation in $m_n$ with wettability, saturation, or both. FIG. 6 shows the plot of $m_n$ as a function of parameter a for data obtained from both of the cores. As expected from equation (7), the slope of the fitted line for each core corresponds to (m−n), and the y-intercept to n. The cementation exponents m of the two cores are identical, and the saturation exponent n for core B is larger than that of core A. These results are consistent with expectations. Since water phase does not form a continuous conductive path, it is expected that the conductivity for a mixed-wet core B is smaller than that for core A at the same water saturation. Consequently, the saturation exponent n is higher and suggests the conclusion that core B is more mixed-wet than core A.

As previously mentioned, in one aspect, it is desirable in obtaining data points for generating determinations of m and n that depth intervals with similar petrophysical properties be identified. Stated differently, in one aspect, it is desirable that in intervals of interest that are analyzed together, that exponents m and n be substantially constant throughout the interval of interest. In one embodiment, this may be accomplished by taking a sufficiently small depth interval. However, it should be appreciated that m and n values in a rock can change quite rapidly both horizontally and vertically throughout a formation since they can be greatly affected by changes in depositional setting and many stages of diagenesis. Thus, in another embodiment, depth intervals may be classified by using any combination of additional logs, lab information or local knowledge in the same or in other wells in the field. For example, image logs can provide textural classification. As another example, the digenetic history of a formation may be known and can be combined with individual log measurements and mineralogical analysis (e.g., spectroscopy or other multi-mineral analysis). In another embodiment, NMR logging information may be utilized. More particularly, in one embodiment, an NMR factor analysis method may be used to find depth intervals (or groups of locations) with similar petrophysical properties, such as pore space and fluid properties. In another embodiment, $T_2$ cutoff-based methods, such as the P3A method, may be used to classify pore spaces so as to find depth intervals (or groups of locations) with similar petrophysical properties.

The factor analysis method for characterizing locations of similar petrophysical properties is disclosed in U.S. Patent Application Publication No. US2014/0114576, published on Apr. 24, 2014, and Jain, V., et al., Characterization of Underlying Pore and Fluid Structure Using Factor Analysis on NMR Data, SPWLA 54th Annual Logging Symposium (Jun. 22-26, 2013), which are both hereby incorporated by reference herein in their entireties. Factor analysis groups together "poro-fluid" distributions. Due to the factors that influence a $T_2$ distribution, these poro-fluid classes should all contain similar pore size distributions as well as similar fluid types. Therefore, the impact of diagenesis and deposition throughout depths associated with a single "poro-fluid" class should have similar m values and similar n values.

Figure 7:
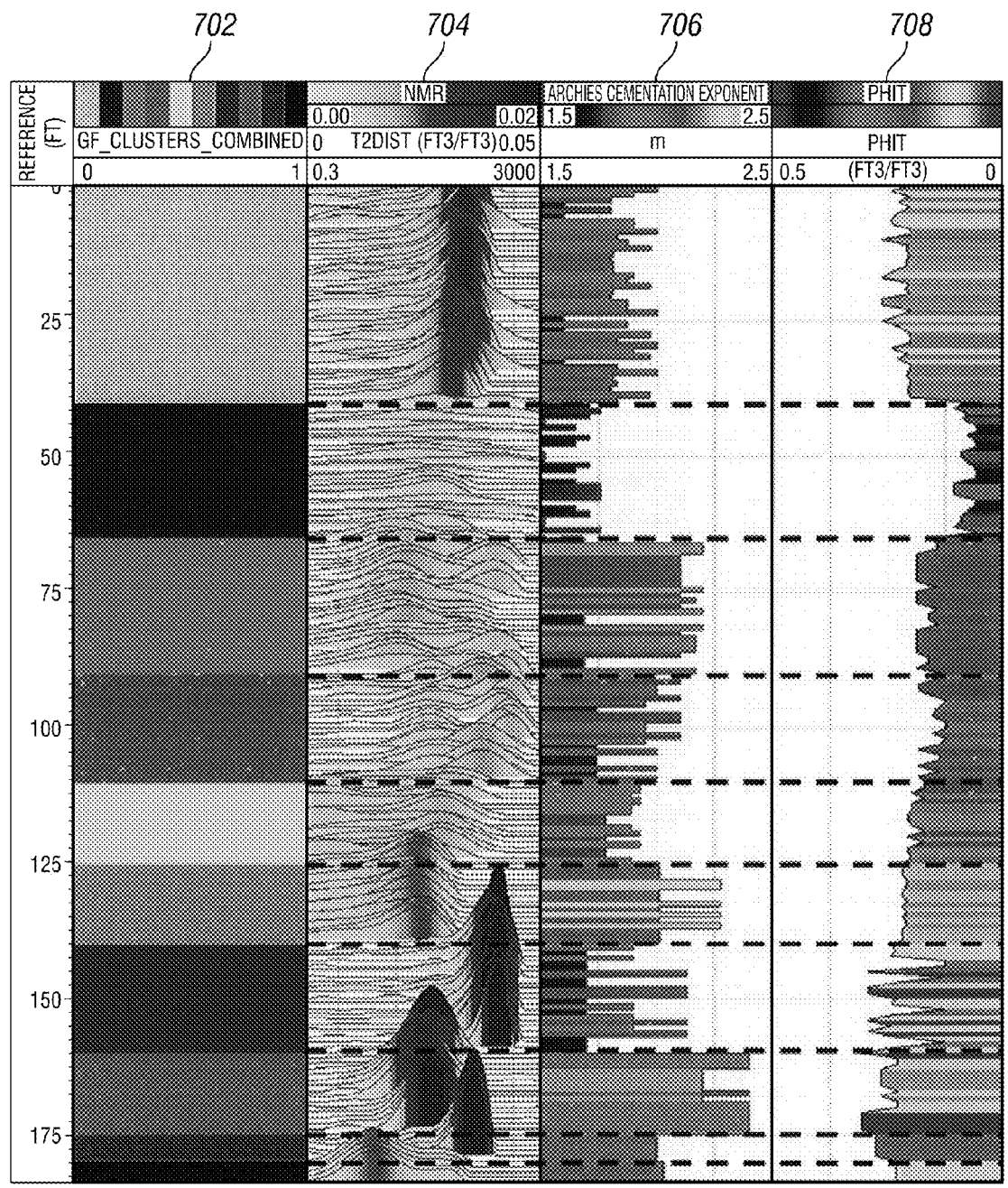
FIG. 7 shows a simulated well log of depth intervals, NMR $T_2$ distributions, cementation exponent, and porosity for a formation, where the depth intervals were determined using a factor analysis method.

FIG. 7 shows a well log of depth intervals (702), NMR $T_2$ distributions (704), cementation exponents (706), and porosities (708) for a formation. The depth intervals were determined based on the NMR $T_2$ distributions using the factor analysis method. The depth intervals are determined so that similar NMR $T_2$ distributions are grouped together. As shown in FIG. 7, the factor analysis method can be used to select depth intervals that have relatively uniform cementation exponents and porosity values within each depth interval.

The P3A method is disclosed in Ramamoorthy, R., et al., A New Workflow for Petrophysical and Textural Evaluation of Carbonate Reservoirs, SPWLA 49th Annual Logging Symposium, (May 25-28, 2008), which is hereby incorporated by reference herein in its entirety. This method uses two user-defined cutoffs to divide the $T_2$ (transverse relaxation) distribution into three pore types: micro-pores, meso-pores and macro-pores. These three pore types are then combined to determine a pore-type classification based on the relative abundance of the three types. Thus, locations (depths) in the wellbore where the abundance of the different pore sizes match may be used to define depth intervals (or groups of locations).

Figure 8:
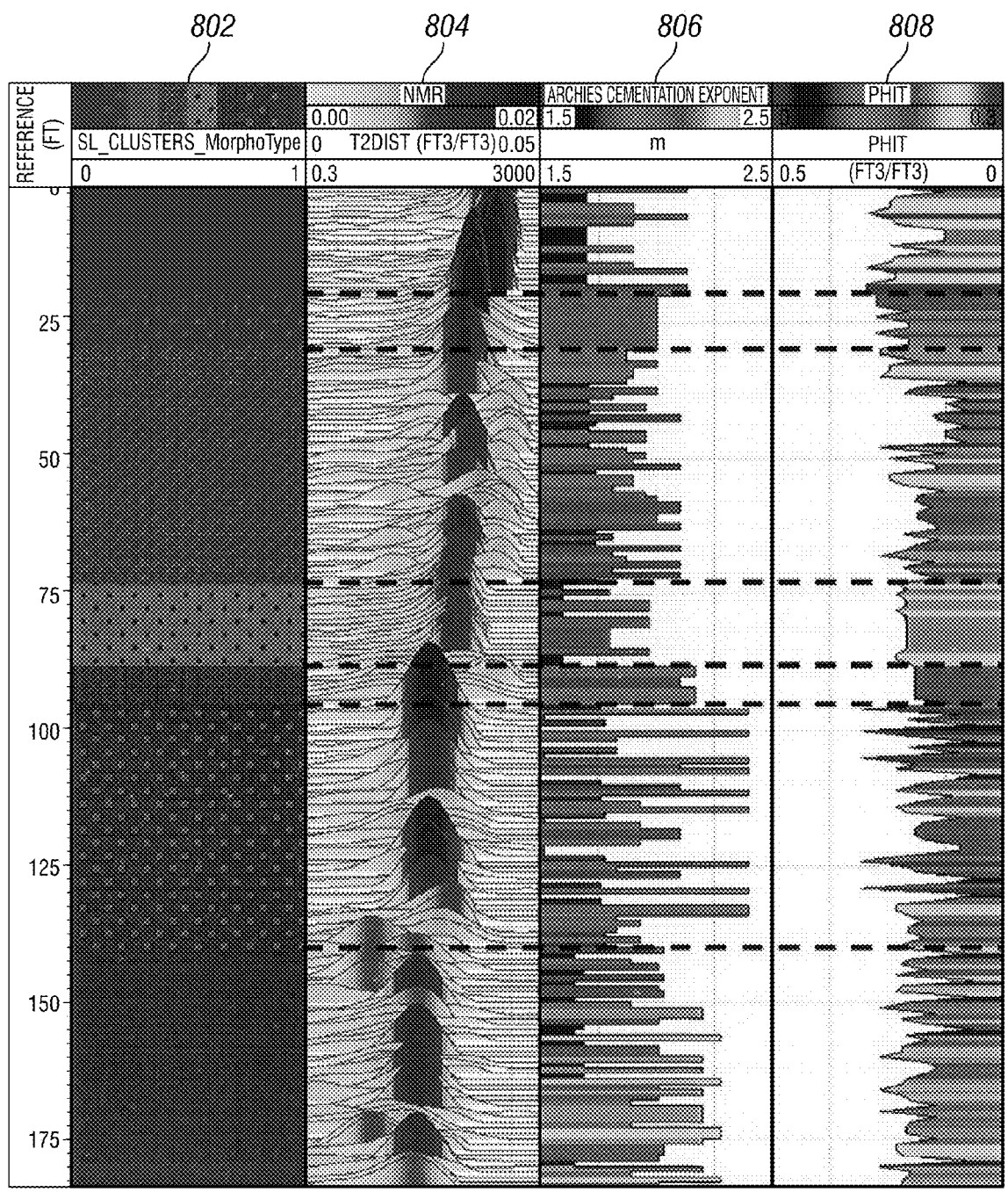
FIG. 8 shows a simulated well log of depth intervals, NMR $T_2$ distributions, cementation exponent, and porosity for a formation, where the depth intervals were determined using a P3A method.

FIG. 8 shows a well log of depth intervals (802), NMR $T_2$ distributions (804), cementation exponents (806), and porosities (808) for a formation. The depth intervals were determined using the P3A method. As shown in FIG. 8, the P3A method can be used to select depth intervals that have relatively uniform cementation exponents and porosity values within each depth interval (albeit with more scatter than the factor analysis method shown in FIG. 7).

In one aspect, it will be appreciated that the depth locations that have similar petrophysical properties as determined by any of the above-mentioned methods do not have to be contiguous. Thus, data from different locations in the wellbore may be grouped together for purposes of generating data points for use in equation (9) or (10) or for analysis such as in FIG. 4.

In one aspect, when solving equations (9) and (10) to obtain m and n values, only the points belonging to a particular class (indicated by index i) are evaluated. In one embodiment, to help reduce uncertainty in the regression, only values with $S_w \leq$ a maximum saturation value, $\phi_i \geq$ a minimum porosity value, $m_n \geq$ a minimum $m_n$ value, and, in the case of equation (10), $w(i) \geq$ a minimum weight are considered. These limiting values can be set as desired but should respect the measurement limits of the tools being utilized (e.g., minimum porosity=5 pu), minimum $m_n$=1.0, minimum weight=0.5), and should consider physically unrealistic values (maximum saturation=1.0 saturation units). Even with this subset of data, it is possible that the regression is not sensitive to the m or n ends of the equation. Therefore, "good" and "bad" limits may be set to the standard deviation. If the standard deviation of m is less than the "good" limit, then the computed m can be trusted for this class (index), and a similar check can be done for the computed n and its standard deviation. If the standard deviation is above the "bad" limit, the data may be considered unreliable, and m or n may not be computed. Thus, a quality control flag may be generated for the output of the computation which indicates whether the results should be ignored (or not provided), whether the results should be taken with caution, or whether the results are believed to be accurate.

In one embodiment, logs of one or both of values of m and n are generated as a function depth or distance in a wellbore. In one embodiment, values of one or both of m and n are used to generate logs of other formation parameters, such as, by way of example and not by way of limitation, wettability or virgin zone saturation.

Figure 9:
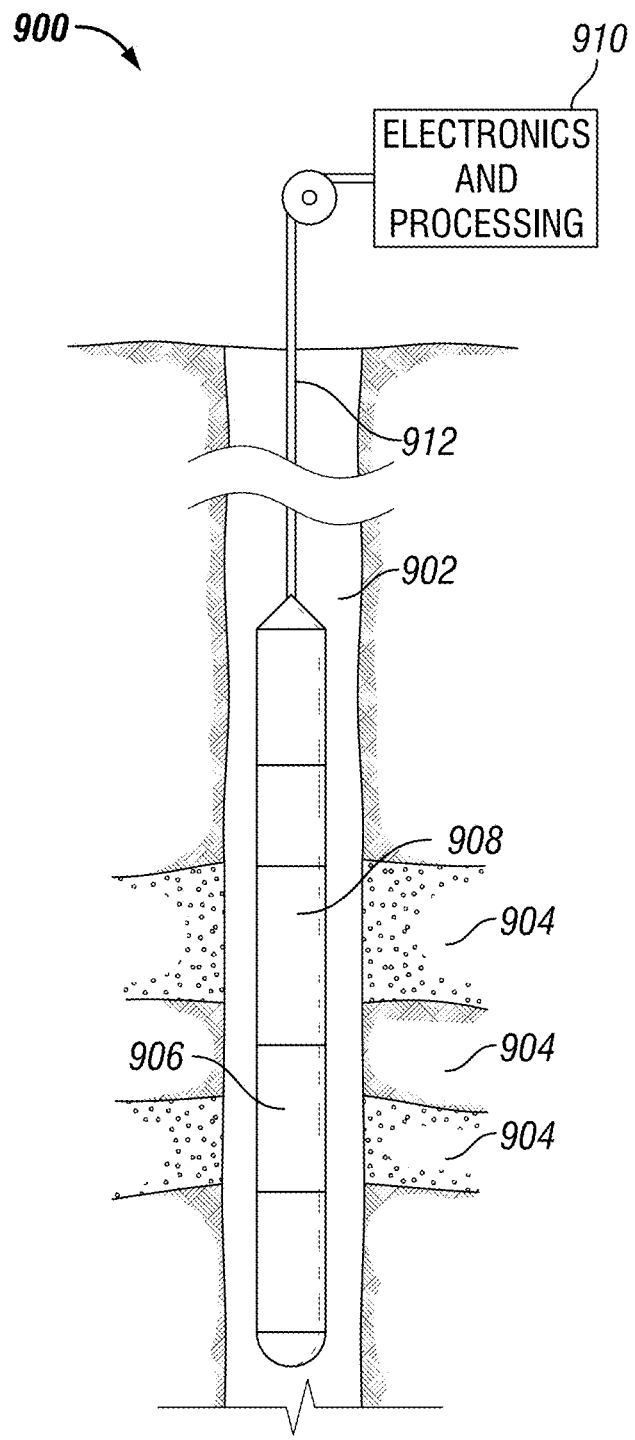
FIG. 9 shows a wellbore logging tool that can be used to acquire data that characterizes a formation.

The formation porosity, formation water saturation, apparent cementation exponent, and NMR data used by the methods described herein can be acquired using a wellbore logging tool, such as a wireline logging tool or a logging-while-drilling (LWD) tool. FIG. 9 shows an example of a wellbore logging tool that can be used to acquire data that characterizes a formation. In this example, the wellbore tool 900 is a wireline tool. The wireline tool 900 is disposed within a wellbore 902 that traverses a formation 904. The wireline tool includes 900 a dielectric tool 906 to perform dielectric measurements of the formation 904 and to obtain dielectric data. This dielectric data can then be used to determine the water saturation and the apparent cementation exponent for the formation. The wireline tool may also include an NMR tool 908 to perform NMR measurements of the formation and to obtain NMR data. This NMR data can then be used to determine the porosity of the formation and/or to group locations within the formation based on similar petrophysical properties. In yet another embodiment, the wireline tool includes a nuclear tool, such as a neutron porosity tool, to gather porosity data for the formation. The wireline tool 900 is coupled to a processing system 910 via a wireline 912. The processing system 910 is located at a surface location. Signals and data that are acquired by the wireline tool 900 are sent from the wireline tool uphole for processing and analysis by the processing system.

In another embodiment, the formation porosity, formation water saturation, apparent cementation exponent, and NMR data used by the methods described herein can be acquired using laboratory measurements. In such an embodiment, a number of formation cores are extracted using a coring tool and/or wellbore cuttings are collected during a wellbore drilling operation. The cores and/or cuttings are analyzed in a laboratory to determine the formation porosity, formation water saturation, apparent cementation exponent, and NMR properties of the formation.

Some of the methods and processes described above, such as the identification of depth intervals with similar petrophysical properties, the calculation of values for parameters such as a(i), and the determination of parameters m and n are performed by a processing system. The term "processing system" should not be construed to limit the embodiments disclosed herein to any particular device type or system. The processing system may include a single processor, multiple processors, or a computer system. The computer system may also include a computer processor (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, Matlab, JAVA or other language or environment). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processing system may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Thus, by way of example only, and not by way of limitation, while various embodiments describe specific tools, such as the Dielectric Scanner™ tool with Dielectric Pro™ software to obtain $m_n$ and $S_w$ values, or CMR-Plus™ tool to obtain NMR data (all trademarks of Schlumberger Technology Corporation), it will be appreciated many other dielectric or NMR tools may be used. Similarly, while certain tools and techniques (such as NMR/P3A or NMR/factor analysis, image logs, spectroscopy, etc.) were described for finding formation depths with similar petrophysical properties, it will be appreciated that other tools and techniques may be utilized. Also, while various embodiments describe obtaining determinations (estimations) of both m and n parameters, it will be appreciated that either parameter may be determined. Further, while specific uses of the estimations of the parameters were described, it will be appreciated that one or both of the parameters may be utilized for other purposes as well. Accordingly, all such modifications are intended to be included within the scope of this disclosure.

What is claimed is:

1. A method for determining values of at least one parameter of a formation to generate an improved virgin zone water saturation, the method comprising:

performing a dielectric measurement of the formation to obtain dielectric data using a dielectric tool included within a wellbore logging tool;

performing a nuclear magnetic resonance (NMR) measurement of the formation to obtain NMR data using an NMR tool included within the wellbore logging tool;

performing a measurement of the formation to obtain formation data using a neutron porosity tool included within the wellbore logging tool;

determining formation porosity $\phi$, formation water saturation $S_w$, and apparent cementation exponent $m_n$ for a plurality of locations in the formation having similar petrophysical properties, wherein the apparent cementation exponent is obtained from dielectric data;

determining an estimation of at least one of a pore cementation exponent m and a saturation exponent n from the formation porosity $\phi$, the formation water saturation $S_w$, and the apparent cementation exponent $m_n$ for the plurality of locations; and calculating an estimated virgin zone water saturation based upon, at least in part, the estimation of the at least one of the pore cementation exponent m and the saturation exponent n.

2. The method of claim 1, wherein at least one of the pore cementation exponent m and the saturation exponent n are determined according to:

$$m_n(i) = (m-n)a(i) + n,$$

where $m_n$ (i) is the estimated $m_n$ at depth i of one of the plurality of locations, and $$a(i) = \frac{\log(\phi(i))}{\log(\phi(i)) + \log(S_w(i))}.$$

3. The method of claim 2, wherein determining at least one of the pore cementation exponent m and the saturation exponent n comprises fitting a line to points on a plot having $m_n$ and a(i) as axes, and finding the saturation exponent n as the intersection of the line to where a(i)=0.

4. The method of claim 2, wherein determining at least one of the pore cementation exponent m and the saturation exponent n comprises fitting a line to points on a plot having $m_n$ and a(i) as axes, and finding the pore cementation exponent m as the intersection of the line to where a(i)=1.

5. The method of claim 2, wherein determining at least one of the pore cementation exponent m and the saturation exponent n comprises finding m and n according to:

$$\begin{bmatrix} \Sigma a^2(i) & \Sigma a(i)(1-a(i)) \\ \Sigma a(i)(1-a(i)) & \Sigma((1-a(i))^2 \end{bmatrix} \begin{bmatrix} m \\ n \end{bmatrix} = \begin{bmatrix} \Sigma a(i) m_n(i) \\ \Sigma(1-a(i))m_n(t) \end{bmatrix}.$$

6. The method of claim 2, wherein determining at least one of the pore cementation exponent m and the saturation exponent n comprises finding m and n according to:

$$\begin{bmatrix} \Sigma w(i)a^2(i) & \Sigma w(i)a(i)(1-a(i)) \\ \Sigma w(i)a(i)(1-a(i)) & \Sigma w(i)((1-a(i))^2 \end{bmatrix}$$

$$\begin{bmatrix} m \\ n \end{bmatrix} = \begin{bmatrix} \Sigma w(i)a(i)m_n(i) \\ \Sigma w(i)(1-a(i))m_n(t) \end{bmatrix}$$

where w(i) are weights.

7. The method of claim 6, wherein the weights are a function of uncertainties associated with values of the cementation exponent $m_n$.

8. The method of claim 1, further comprising using the pore cementation exponent m and the saturation exponent n to estimate virgin zone water saturation according to $\sigma = \phi^m S_w^n \sigma_w$, where σ is a measured conductivity of partially saturated rock at the plurality of locations and $\sigma_w$ is the direct current conductivity of water at the plurality of locations.

9. The method of claim 1, wherein the plurality of locations having similar petrophysical properties are determined using nuclear magnetic resonance (NMR) log information.

10. The method of claim 9, wherein said NMR log information is $T_2$ transverse relaxation information.

11. A method for determining values of at least one parameter of a formation to generate an improved virgin zone water saturation, the method comprising:
performing a dielectric measurement of the formation to obtain dielectric data using a dielectric tool included within a wellbore logging tool;
performing a nuclear magnetic resonance (NMR) measurement of the formation to obtain NMR data using an NMR tool included within the wellbore logging tool;
performing a measurement of the formation to obtain formation data using a neutron porosity tool included within the wellbore logging tool;
determining formation porosity φ, formation water saturation $S_w$, and apparent cementation exponent $m_n$ for a plurality of locations in the formation having similar petrophysical properties;
determining an estimation of at least one of a pore cementation exponent m and a saturation exponent n from the formation porosity φ, the formation water saturation $S_w$, and the apparent cementation exponent $m_n$ for the plurality of locations according to: $m_n(i)=(m-n)a(i)+n$, where $m_n(i)$ is the estimated $m_n$ at depth i which is one of the plurality of locations, and $$a(i) = \frac{\log(\phi(i))}{\log(\phi(i)) + \log(S_w(i))}; \text{ and}$$

calculating an estimated virgin zone water saturation based upon, at least in part, the estimation of the at least one of the pore cementation exponent m and the saturation exponent n.

12. A method according to claim 11, wherein determining at least one of the pore cementation exponent m and the saturation exponent n comprises finding m and n according to:

$$\begin{bmatrix} \Sigma a^2(i) & \Sigma a(i)(1-a(i)) \\ \Sigma a(i)(1-a(i)) & \Sigma((1-a(i))^2 \end{bmatrix} \begin{bmatrix} m \\ n \end{bmatrix} = \begin{bmatrix} \Sigma a(i)m_n(i) \\ \Sigma(1-a(i))m_n(t) \end{bmatrix}.$$

13. The method of claim 11, wherein determining at least one of the pore cementation exponent m and the saturation exponent n comprises finding m and n according to:

$$\begin{bmatrix} \Sigma w(i)a^2(i) & \Sigma w(i)a(i)(1-a(i)) \\ \Sigma w(i)a(i)(1-a(i)) & \Sigma w(i)((1-a(i))^2 \end{bmatrix}$$

$$\begin{bmatrix} m \\ n \end{bmatrix} = \begin{bmatrix} \Sigma w(i)a(i)m_n(i) \\ \Sigma w(i)(1-a(i))m_n(t) \end{bmatrix}$$

where w(i) are weights which are a function of uncertainties associated with values of the apparent cementation exponent $m_n$.

14. The method of claim 11, further comprising using the pore cementation exponent m and the saturation exponent n to estimate virgin zone water saturation according to $\sigma = \phi^m S_w^n \sigma_w$, where σ is a measured conductivity of partially saturated rock at the plurality of locations, and $\sigma_w$ is the direct current conductivity of water at the plurality of locations.

15. The method of claim 11, wherein the plurality of locations having similar petrophysical properties are determined using nuclear magnetic resonance (NMR) log information.

16. A method for determining values of parameters of a formation traversed by a wellbore to generate an improved virgin zone water saturation, the method comprising:
performing a dielectric measurement of the formation to obtain dielectric data using a dielectric tool included within a wellbore logging tool;
performing a nuclear magnetic resonance (NMR) measurement of the formation to obtain NMR data using an NMR tool included within the wellbore logging tool;
determining formation water saturation $S_w$ and an apparent cementation exponent $m_n$ for multiple locations in the formation along the wellbore using the dielectric data;

performing a measurement of the formation to obtain formation data using a neutron porosity tool included within the wellbore logging tool;

determining formation porosity for the multiple locations in the formation along the wellbore using the formation data;

grouping the multiple locations in the formation into a plurality of groups of locations having similar petrophysical properties;

for each group of the plurality of groups, determining at least one a pore cementation exponent m and a saturation exponent n for that group of locations using the formation porosity, formation water saturation $S_w$, and the apparent cementation exponent $m_n$; and calculating an estimated virgin zone water saturation based upon, at least in part, the estimation of the at least one of the pore cementation exponent m and the saturation exponent n.

17. The method of claim 16, wherein at least one of the pore cementation exponent m and the saturation exponent n are determined according to:

$$m_n(i)=(m-n)a(i)+n$$

where $m_n(i)$ is the estimated $m_n$ for group i, and $$a(i) = \frac{\log(\phi(i))}{\log(\phi(i)) + \log(S_w(i))}.$$

18. The method of claim 17, wherein determining at least one of the pore cementation exponent m and the saturation exponent n comprises finding m and n according to:

$$\begin{bmatrix} \Sigma a^2(i) & \Sigma a(i)(1-a(i)) \\ \Sigma a(i)(1-a(i)) & \Sigma((1-a(i))^2 \end{bmatrix} \begin{bmatrix} m \\ n \end{bmatrix} = \begin{bmatrix} \Sigma a(i)m_n(i) \\ \Sigma(1-a(i)m_n(t) \end{bmatrix}.$$

19. The method of claim 17, wherein determining at least one of the pore cementation exponent m and the saturation exponent n comprises finding m and n according to:

$$\begin{bmatrix} \Sigma w(i)a^2(i) & \Sigma w(i)a(i)(1-a(i)) \\ \Sigma w(i)a(i)(1-a(i)) & \Sigma w(i)((1-a(i))^2 \end{bmatrix}$$

$$\begin{bmatrix} m \\ n \end{bmatrix} = \begin{bmatrix} \Sigma w(i)a(i)m_n(i) \\ \Sigma w(i)(1-a(i)m_n(t) \end{bmatrix}$$

where w(i) are weights that are a function of uncertainties associated with values of the apparent cementation exponent $m_n$.

20. The method of claim 16, wherein the plurality of groups of locations having similar petrophysical properties are grouped using the NMR data.

* * * * *